United States Patent [19]

Crutchfield et al.

[11] 4,144,324

[45] Mar. 13, 1979

[54] ORAL COMPOSITIONS FOR CALCULUS RETARDATION

[75] Inventors: Marvin M. Crutchfield, St. Louis; Keun Y. Kim, Chesterfield, both of Mo.

[73] Assignee: Colgate Palmolive Company, New York, N.Y.

[21] Appl. No.: 931,697

[22] Filed: Aug. 7, 1978

Related U.S. Application Data

[60] Continuation of Ser. No. 730,930, Oct. 8, 1976, abandoned, which is a continuation of Ser. No. 627,987, Nov. 3, 1975, abandoned, which is a division of Ser. No. 549,647, Feb. 13, 1975, abandoned, which is a division of Ser. No. 386,121, Aug. 6, 1973, abandoned, which is a continuation-in-part of Ser. No. 198,439, Nov. 12, 1977, abandoned.

[51] Int. Cl.$^2$ .............................................. A61K 7/22
[52] U.S. Cl. ....................................................... 424/54
[58] Field of Search ................................. 424/48-58

[56] References Cited

U.S. PATENT DOCUMENTS

| Re. 29,182 | 4/1977 | McCune et al. ................ 424/49 |
| --- | --- | --- |
| 3,288,846 | 11/1966 | Irani et al. ...................... 260/502.5 |
| 3,298,956 | 1/1967 | Irani et al. .................. 260/502.5 X |
| 3,336,221 | 8/1967 | Ralston ....................... 260/502.5 X |
| 3,434,969 | 3/1969 | Ralston ....................... 260/502.5 X |
| 3,639,569 | 2/1972 | Medcalf ............................... 424/48 |
| 3,671,644 | 6/1972 | Irani et al. ..................... 424/329 X |
| 3,792,152 | 2/1974 | Kim ..................................... 423/311 |
| 3,832,396 | 8/1974 | Irani et al. ..................... 260/546 P |

FOREIGN PATENT DOCUMENTS

| 1617729 | 8/1971 | Fed. Rep. of Germany. |
| --- | --- | --- |
| 1515665 | 3/1968 | France. |

OTHER PUBLICATIONS

Monsanto Brochure, Dequest* Organophosphorus Compounds (Feb. 1971)

Briner et al., Calc. Tiss. Res. 7: 249-256 (1971) "Factors Affecting the Rate of Post-Eruptive Maturation of Dental Enamel".

Meyer and Nancollas, Calc. Tiss. Res. 13: 295-303 (1973) The Influence of Multidentate Organic Phosphonates on the Crystal Growth of Hydroxyapatite.

*Primary Examiner*—Shep K. Rose

[57] ABSTRACT

Oral compositions, such as foods, toothpaste, mouthwash, and the like, containing certain polyamine polyphosphonates as herein defined which retard dental calculus formation without damaging tooth structure.

6 Claims, No Drawings

ORAL COMPOSITIONS FOR CALCULUS RETARDATION

This is a continuation, of application Ser. No. 730,930 filed Oct. 8, 1976; which is a continuation of application Ser. No. 627,987, filed Nov. 3, 1975, now abandoned; which is a divisional of application Ser. No. 549,647, filed Feb. 13, 1975, now abandoned; which is a divisional of application Ser. No. 386,121, filed Aug. 6, 1973, now abandoned; which is a continuation in part of application Ser. No. 198,439, filed Nov. 12, 1971, all now abandoned.

The field of this invention is "oral compositions" which term is used herein to designate products which are introduced into the oral cavity for a time sufficient to contact substantially all of the exposed dental surfaces. Such products include, for example, animal and human foods and oral hygiene products such as dentifrices, mouthwashes, prophylaxis pastes and topical solutions.

Dental calculus, or tartar as it is sometimes called, is a deposit which forms on the surfaces of the teeth at the gingival margin. Supragingival calculus appears principally in the area near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agency. In addition to being unsightly and undesirble from an aesthetic standpoint, the mature calculus deposits are constant sources of irritation of the gingiva and thereby are a contributing factor to gingivitis and other diseases of the supporting structures of the teeth, the irritation decreasing the resistance of tissues to endogenous and exogenous organisms.

A wide variety of chemical and biological agents have been suggested in the art to retard calculus formation or to remove calculus after it is formed. Mechanical removal of this material periodically by the dentist is, of course, routine dental office procedure.

SUMMARY OF THE INVENTION

It has now been discovered that certain polyamine polyphosphonates possess the surprising capacity to retard the development of dental calculus in humans and lower animals without removing calcium from dental enamel or otherwise damaging the tooth structure when employed in oral compositions maintained within defined pH limits.

Unlike inorganic polyphosphates such as pyrophosphates, the polyamine polyphosphonates employed in the compositions of this invention resist hydrolysis in aqueous products and therefore remain in an active form throughout the normal shelf-life of such products.

DETAILED DESCRIPTION OF THE INVENTION

This invention is an oral composition effective in inhibiting the formation of dental calculus without adversely affecting the tooth structure comprising (1) from about 0.01% to about 10% by weight of a polyamine polyphosphonic acid compound selected from the group consisting of those of the formula:

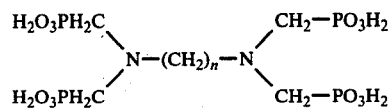

wherein n is a number from 1 to 10 or a pharmaceutically acceptable water soluble salt thereof, such as alkali metal (e.g., sodium and potassium), and ammonium or low molecular weight substituted ammonium (e.g., mono- di- and tri-ethanolammonium) salts; and (2) a carrier suitable for use in the oral cavity of humans and lower animals, the pH of said composition being in the range from about 5.0 to 11.0. The above described polyamine polyphosphonic acids and their pharmaceutically acceptable salts are referred to collectively herein as "polyamine polyphosphonates".

Operable polyamine polyphosphonates include ethylenediamine tetra(methylene phosphonic acid), penta methylene diamine tetra(methylene phosphonic acid), hexamethylene diamine tetra(methylene phosphonic acid), octamethylene diamine tetra(methylenephosphonic acid) and the water soluble pharmaceutically acceptable salts of these acids, e.g., sodium, potassium and ammonium salts.

The most preferred polyamine polyphosphonate is ethylene diamine tetra(methylene phosphonic acid) and its water soluble pharmaceutically acceptable salts, particularly the sodium salts.

Mixtures of any of the foregoing polyamine polyphosphonates can be used in the practice of this invention.

The polyamine polyphosphonates and suitable salts thereof can be prepared in any convenient manner. For example, according to the teachings of U.S. Pat. No. 3,288,846, which is incorporated herein by reference.

The dental calculus inhibiting concentration of polyamine polyphosphonates in the oral compositions of this invention can range widely. There is no upper limit on the amount that can be utilized except as dictated by cost or incompatibility with the carrier. However, an amount below 0.01% by weight generally does not satisfactorily retard dental calculus. Generally, concentrations from 0.01% to about 10% by weight are utilized. Oral compositions which in the ordinary course of usage may be accidentally or intentionally ingested can contain lower concentrations of polyamine polyphosphonates. Of course, any such polyamine polyphosphonates should be physiologically acceptable. Thus, a mouthwash in accordance with this invention preferably contains less than about 3% by weight of polyamine polyphosphonate. Dentifrice compositions, topical solutions and prophylaxes pastes, the latter to be administered professionally, can contain up to about 10% by weight, preferably from about 0.1% to about 5.0% by weight of polyamine polyphosphonate and still more preferably from about 1 to 2% by weight.

The pH of the composition of this invention can range from about 5.0 to about 11. Below about pH 5.0 damage to the dental enamel can occur in spite of the relative safety of the polyamine polyphosphonates. Above about pH 11.0, difficulty is encountered in formulating products having satisfactory flavor and mildness. A preferred pH range is from about 7.0 to about 10. The pH of the composition, of course, is determinative of the predominate salt form of the polyamine polyphosphonates present therein.

While it is not intended that this invention be limited by a particular theory of operation, it has been observed that the water soluble polyamine polyphosphonates encompassed herein interfere with the progress of calculus formation by interfering with the conversion of amorphous calcium phosphate to crystalline calcium hydroxyapatite. Amounts of polyamine polyphosphonates which are much too small to chelate any appreciable quantities of calcium have been found to retard the formation of calcium hydroxyapatite. This selective action on the formative calculus deposits without demineralizing action on the dental enamel is surprising.

As hereinbefore stated, the polyamine polyphosphonates inhibit the growth of calcium hydroxyapatite crystals and in this way interfere with the normal formation of calcium hydroxyapatite from solution. This interference is demonstrated by a test designed to determine the effect of polyamine polyphosphonates on the formation of calcium phosphate on addition of orthophosphate ion to calcium ion at a constant pH in an environment designed to correspond to natural saliva. The inorganic components of saliva are described extremely well in a recent book, *Art And Science of Dental Caries Research*, Academic Press, New York and London, Chapter VI. Table I summarizes the inorganic composition of saliva adapted from this book and the concentrations for this test.

having a pH adjusted to 7 by sodium hydroxide) was added to a volume of deionized water to yield 100 milliliters of final volume. To this was added one milliliter of 0.005 M ethylene diamine tetra(methylene phosphonic acid) solution to provide 23 parts per million of said phosphonate and then 5 milliliters of a phosphate solution containing 1 M of $K_2HPO_3.3H_2O$ and having pH adjusted to 7 by hydrochloric acid. Another test was made with the exception that for the above phosphonate was substituted hexamethylene diamine tetra(methylene phosphonic acid) to provide about 25 parts per million of said phosphonate. A control was also run in which no phosphonate was added. The samples were incubated at a temperature of 37° C. Precipitation behavior was observed for 3 hours. In the container containing the control, the solution became cloudy first, then calcium phosphate started to precipitate in 10 to 20 minutes and coagulated to a fine precipitate in 2 hours. In the container in which the phosphonate was present, the mixture did not produce a precipitate and was stable for many days.

After three hours, each of the solutions which contained precipitate was filtered through a 0.45 μ millipore filter pad. The precipitate was air dried and analyzed by X-ray diffraction. The solid calcium phosphate precipitated from the above-described control solution without a polyamine polyphosphonate gives a poorly crystalline hydroxyapatite pattern. Chemical analysis shows an atom ratio of Ca to P of 1.2–1.3. This is intermediate between the atom ratio found in dicalcium phosphate (1.0) and that found in hydroxyapatite (1.07) and approximate to the Ca to P ratio found in dental plaque. By the use of a polyamine polyphosphonate, the formation of plaque-like precipitate, was inhibited.

Oral hygiene products are illustrative of some of the embodiments of this invention. These can be dentifrices, mouthwashes, prophylaxis pastes and topical solutions.

TABLE I

| | INORGANIC COMPOSITION OF SALIVAS (millimoles/liter) | | | | |
|---|---|---|---|---|---|
| | Parotid Saliva | | Submandibular Saliva | | Concentration |
| Component | Unstimulated | Stimulated | Unstimulated | Stimulated | |
| Ca | 1.3 | 1.6 | 2.1 | 2.4 | 2.0 |
| P | 8.0 | 3.2 | 6.0 | 3.3 | 5.0 |
| Mg | 0.1 | 0.02 | 0.08 | 0.03 | — |
| Na | 2.5 | 35.0 | 10 | 25 | 20 |
| K | 37.0 | 21.0 | 17 | 14 | 20 |
| Cl | 33.0 | 32.0 | 25 | 25 | 36 |
| $HCO_3$ | 1.0 | 20.0 | 4 | 25 | — |
| pH | 5.5 | 7.4 | 6.4 | 7.4 | 7.0 |
| ionic strength* | 49.6 | 61.2 | 39.7 | 48.4 | 48 |

*assumed 1:1 distribution of $HPO_4^{--}$ and $H_2PO_4^=$ at pH 7.0

The composition of saliva varies greatly with the source (parotid or submantibular glands), the state (unstimulated or stimulated) and flow rate (depending upon the degree of stimulation). The major inorganic components of saliva are calcium, phosphorus, sodium, potassium, chloride, bicarbonate and dissolved carbon dioxide. Since calcium salts precipitate under dynamic conditions in the mouth, arithmetic averages of the values given in Table I for the respective elements were employed in this study as representative ion concentrations in saliva. Only the chloride and phosphate forms were used in the preparation of stock solution to provide the required elements. The carbonate was not added. The ionic strength of the simulated chemical environment was 48 millimoles/liter.

Two milliliters of a calcium stock solution (containing 0.1 M $CaCl_2.2H_2O$, 1 M NaCl, and 0.5 M KCl and A dentifrice, especially toothpaste, containing a polyamine polyphosphonate is a preferred embodiment of this invention. Toothpaste compositions conventionally contain abrasive materials, sudsing agents, binders, humectants, flavoring and sweetening agents.

The abrasive materials and other adjuncts used in the practice of this invention are preferably not sources of much soluble calcium so that the crystal growth inhibiting capacity of the polyamine polyphosphonate is not depleted to an extent that its anticalculus activity is impaired. Thus, conventional abrasives such as dicalcium orthophosphate dihydrate and calcium carbonate are preferably not used. However, predominantly β-phase calcium pyrophosphate prepared in accordance with the teachings of Schweizer, U.S. Pat. No. 3,112,247, granted Nov. 26, 1963, or dicalcium orthophosphate anhydrous which contain relatively little soluble calcium can be used. An especially preferred class of abrasives for use herein are the particulate thermosetting polymerized resins as described by Cooley et al in U.S. Pat. No. 3,070,510, granted Dec. 25, 1962. Suitable resins include, for example, melamines, phenolics, ureas, melamine-ureas, melamine-formaldehydes, urea-formaldehydes, melamine-urea-formaldehydes, cross-linked epoxides, and cross-linked polyesters.

Other abrasives include alumina, the insoluble non-calcium metaphosphates such as sodium metaphosphate, the silica xerogels and alumina-silicates. Mixtures of abrasives can also be used. In any case, the total amount of abrasive in the dentifrice embodiments of this invention can range from 0.5% to 95% by weight of the dentifrice. Preferably, toothpastes contain from 20% to 60% by weight of abrasive. Abrasive particle size preferably ranges from 2 microns to 20 microns.

Suitable sudsing agents are those which are reasonably stable and form suds throughout a wide pH range, preferably nonsoap anionic organic synthetic detergents. Examples of such agents are water-soluble salts of alkyl sulfate having from 10 to 18 carbon atoms in the alkyl radical, such as sodium lauryl sulfate; water-soluble salts of sulfonated monoglycerides of fatty acids having from 10 to 18 carbon atoms, such as sodium monoglyceride sulfonates; salts of $C_{10}$-$C_{18}$ fatty acid amides of taurine, such as sodium N-methyl-N-palmitoyl tauride; salts of $C_{10}$-$C_{18}$ fatty acid esters of isethionic acid; and substantially saturated aliphatic acyl amides of saturated mono-aminocarboxylic acids having 2 to 6 carbon atoms and in which the acyl radical contains 12 to 16 carbon atoms, such as sodium N-lauroyl sarcoside. Mixtures of two or more sudsing agents can be used.

The sudsing agent can be present in the dentifrice compositions of this invention in an amount of 0.5% to 5% by weight of the total composition.

In preparing toothpastes, it is necessary to add some thickening material to provide a desirable consistency. Preferred thickening agents are hydroxyethyl cellulose and watersoluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. Thickening agents in an amount from 0.5% to 5.0% by weight of the total composition can be used.

It is also desirable to include some humectant material in a toothpaste to keep it from hardening. Suitable humectants include glycerine, sorbitol, and other edible polyhydric alcohols. The humectant can comprise up to about 36% by weight of the toothpaste composition.

Suitable flavoring agents include oil of wintergreen, oil of peppermint, oil of spearmint, oil of sassafras, and oil of clove. Sweetening agents which can be used include saccharin, dextrose, levulose and sodium cyclamate.

Several representative oral compositions illustrating this invention are set forth in the following examples.

EXAMPLE I

A toothpaste of the following composition is prepared by conventional methods:

|  | Parts by Weight |
| --- | --- |
| Water | 31.58 |
| Sorbitol | 6.25 |
| Saccharin | 0.12 |
| Calcium pyrophosphate* | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Magnesium aluminum silicates | 0.40 |
| Flavoring | 0.85 |
| Ethylene diamine tetra(methylene phosphonic acid) | 1.50 |
| pH - 5.90 | |

*Prepared in accordance with U.S. Pat. 3,112,247 granted November 26, 1963.

A toothpaste composition substantially identical to the composition of Example I is prepared with methylene diamine tetra(methylene phosphonic acid) respectively rather than ethylene diamine tetra(methylene phosphonic acid).

EXAMPLE II

Yet another toothpaste is prepared having the following compositions:

|  | Parts by Weight |
| --- | --- |
| Water | 39.50 |
| Sorbitol | 6.25 |
| Saccharin | .12 |
| Abrasive (precipitated urea/formaldehyde condensate) | 31.00 |
| Glycerine | 18.00 |
| Sodium alkyl (coconut) sulfate | .42 |
| Sodium coconut monoglyceride sulfonate | .75 |
| Sodium carboxymethyl cellulose | 1.15 |
| Magnesium aluminum silicate | .40 |
| Flavoring | .95 |
| Hexamethylene diamine tetra(methylene phosphonic acid) | 1.50 |
| pH - 5.3 | |

Several additional toothpastes are prepared having essentially the same composition as the toothpaste of Example II, but using the disodium salt of hexamethylene diamine tetra(methylene phosphonic acid); the trisodium salt of hexamethylene diamine tetra(methylene phosphonic acid); the disodium salt of ethylene diamine tetra(methylene phosphonic acid); the monopotassium salt of ethylene diamine tetra(methylene phosphonic acid); the tetrasodium salt of hexamethylene diamine tetra(methylene phosphonic acid). The pH of these compositions is adjusted to 7.0. These toothpaste formulations effectively retard calculus formation on dental enamel without decalcifying same.

Several mouthwash compositions are prepared in accordance with this invention as follows:

| Component | Example (Parts by Weight) | | | |
| --- | --- | --- | --- | --- |
|  | III | IV | V | VI |
| Glycerine | 10.0 | 10.0 | 10.0 | 10.0 |
| Ethyl alcohol | 16.5 | 16.5 | 16.5 | 16.5 |
| Water | 67.172 | 67.172 | 67.172 | 70.192 |
| Tween 80[1] | .12 | .12 | .12 | .12 |
| Saccharin | .045 | 0.45 | 0.45 | .02 |
| Sodium cyclamate | .075[1] | .075 | .075 | .04 |
| Flavor | .088 | .088 | .088 | .088 |
| Polyamine polyphosphonate | 3.0[2] | 3.0[3] | 3.0[4] | 1.0[5] |
| pH | 7.0 | 8.5 | 10.0 | 10.0 |

[1] Polyoxyethylene (20 moles of ethylene oxide) sorbitan monooleate, ammonionic emulsifier supplied by Atlas Powder Co.
[2] Hexamethylene diamine tetra(methylene phosphonic acid).
[3] Ethylene diamine tetra(methylene phosphonic acid).
[4] Hexamethylene diamine tetra(methylene phosphonic acid).
[5] Ethylene diamine tetra(methylene phosphonic acid).

Mouthwash compositions corresponding to Example V are prepared, substituting the dipotassium salt of hexamethylene diamine tetra(methylene phosphonic acid), the dipotassium salt of hexamethylene diamine tetra(methylene phosphonic acid), the tetrasodium salt of ethylene diamine tetra(methylene phosphonic acid) for the hexamethylene diamine tetra(methylene phosphonic acid) and adjusting the pH to 8.0.

EXAMPLE VII

A prophylaxis paste for use by the dentist for removal of stains and polishing the teeth after mechanical removal of calculus deposits is formulated as follows:

|  | Parts by Weight |
|---|---|
| Navajo pumice | 77.10 |
| TiO$_2$ | 4.00 |
| Glycerine | 17.75 |
| Hydroxyethylcellulose | .22 |
| Saccharin | .33 |
| Trisodium salt of hexamethylene diamine tetra(methylene phosphonic acid) | 8.0 |
| pH - 8.0 | |

The prophylaxis paste set forth above is modified by replacing the trisodium salt of hexamethylene diamine tetra(methylene phosphonic acid) with the trisodium salt of ethylene diamine tetra(methylene phosphonic acid), the trisodium salt of hexamethylene diamine tetra(methylene phosphonic acid) and the ethylene diamine tetra(methylene phosphonic acid) respectively.

Toothpowders and the like can be prepared by conventional methods and containing, in addition to the usual ingredients, an amount of polyamine polyphosphonate within the ranges specified herein.

Those components other than polyamine polyphosphonates which were included in the foregoing examples and various mixtures of those components are illustrative of carriers suitable for use in the oral cavity.

Other illustrative embodiments are foods to be ingested by humans and lower animals provided that the polyamine polyphosphonates utilized are physiologically acceptable.

In the reference to pH adjustments in the foregoing examples, it is to be understood that a base of a cation corresponding to the salt form of the polyamine polyphosphonate employed is used to adjust to higher pH value. In case the polyamine polyphosphonate is added in its acid form to the example compositions, the pH can be adjusted to the specified higher value with NaOH. Adjustment in pH to more acid levels can be accomplished with HCl acid. It will be obvious to those skilled in the art that pH adjustments can be made with any acid or base suitable for use in the oral cavity.

What is claimed is:

1. A process for the intentional ingestion of an oral composition which is ingested with contact with exposed dental surfaces by humans or lower animals and which is effective in inhibiting the formation of dental calculus without adversely affecting tooth structure comprising intentionally ingesting a dental calculus inhibiting amount effective in amounts much too small to chelate any appreciable quantities of calcium, to retard the conversion of amorphous calcium phosphate to crystalline calcium hydroxyappatite, which amount is about 0.01% to about 10% by weight, of a physiologically acceptable polyamine polyphosphonate selected from the group consisting of those of the formula:

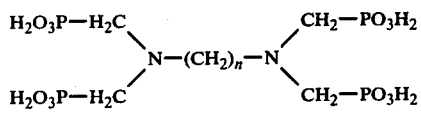

wherein n is a number from 1 to 10, or a pharmaceutically acceptable water soluble salt thereof selected from the group consisting of alkali metal, ammonium and mono-, di- and tri-ethanolammonium salts; the pH of the oral composition being within the range of at least about 5.0 to about 11.0, in order to thereby avoid occurrence of damage to dental enamel below about pH 5.0 and in order to retard the development of dental calculus without removing calcium from dental enamel or otherwise damaging the tooth structure; said oral composition being free of sources of calcium which would yield enough soluble calcium to significantly impair the anticalculus activity of said polyphosponate.

2. The process according to claim 1 wherein said oral composition is a food.

3. The process according to claim 2 wherein said polyamine polyphosphonate is ethylene diamine tetra (methylene phosphonic acid) or a pharmaceutically acceptable water-soluble salt thereof.

4. The process according to claim 2 wherein said polyamine polyphosphonate is hexamethylene diamine tetra (methylene phosphonic acid) or a pharmaceutically acceptable water-soluble salt thereof.

5. The process according to claim 2 wherein said food is ingested by humans.

6. The process according to claim 2 wherein said food is ingested by lower animals.

* * * * *